Figure 1:
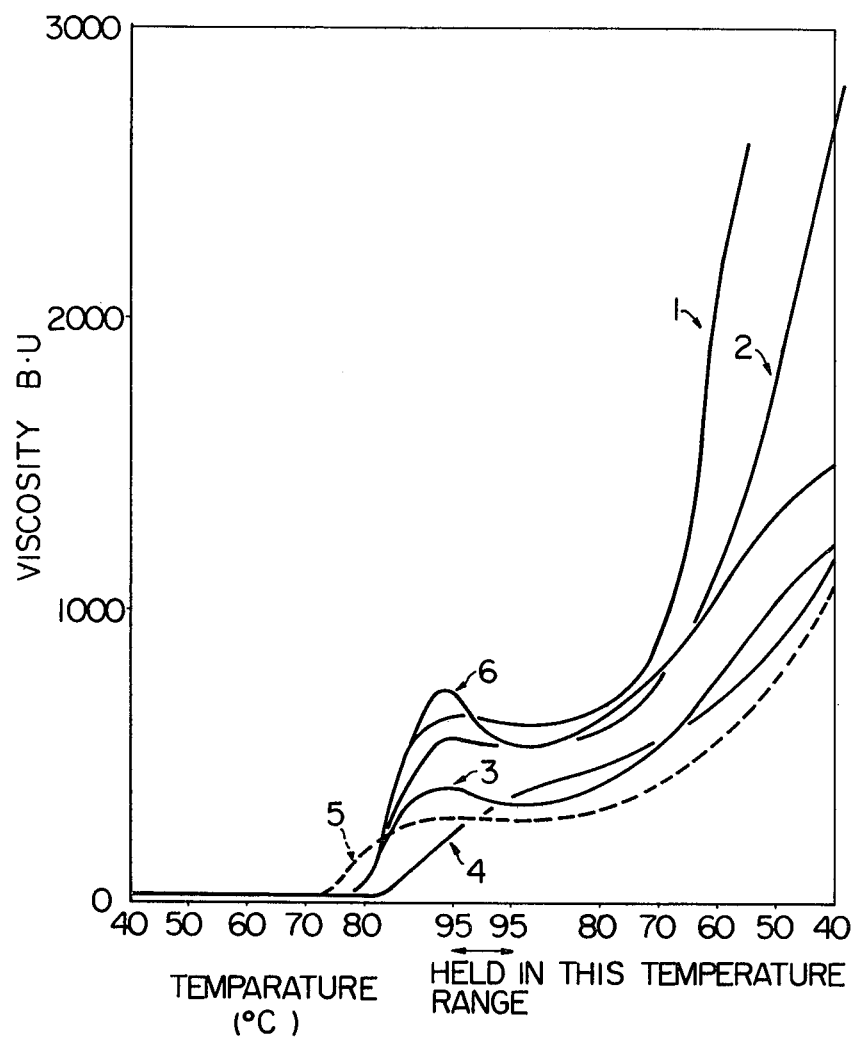

United States Patent [19]

Yoshizumi et al.

[11] 4,092,434

[45] May 30, 1978

[54] PREPARATION OF ALCOHOL OR ALCOHOLIC BEVERAGES

[75] Inventors: Hajime Yoshizumi, Takatusuki; Nobuya Matsumoto; Osamu Fukushi, both of Ibaragi, all of Japan

[73] Assignee: Suntory Ltd., Osaka, Japan

[21] Appl. No.: 632,254

[22] Filed: Nov. 17, 1975

[30] Foreign Application Priority Data

Nov. 26, 1974 Japan ................................ 49-136813

[51] Int. Cl.² .......................... C12C 7/04; C12C 11/08
[52] U.S. Cl. ....................................... 426/13; 195/15; 426/14; 426/29; 426/494
[58] Field of Search ....................... 426/11, 14, 28, 29, 426/494, 13, 16; 195/15, 21

[56] References Cited

U.S. PATENT DOCUMENTS

| | | | |
|---|---|---|---|
| 2,198,221 | 4/1940 | Musher | 426/14 |
| 2,222,306 | 11/1940 | Atwood | 426/13 |
| 2,375,189 | 5/1945 | Blankmeyer et al. | 195/16 |
| 2,790,718 | 4/1957 | Nugey | 426/29 |
| 3,022,174 | 2/1962 | Wimmer et al. | 426/29 |

Primary Examiner—David M. Naff
Attorney, Agent, or Firm—Flynn & Frishauf

[57] ABSTRACT

Alcohol or an alcoholic beverage is produced by a process wherein a mash of cereal grains and liquefying enzymes is cooked at a temperature of from 75° C to 85° C which is lower than the temperature of maximum viscosity for the mash and which is higher than the sterilization temperature of undesirable microorganisms in the mash which grow during fermentation with yeast. After cooking, the mash is cooled, saccharifying enzymes are added, the resultant mash is fermented with yeast to produce alcohol and the alcohol is distilled.

8 Claims, 1 Drawing Figure

PREPARATION OF ALCOHOL OR ALCOHOLIC BEVERAGES

This invention relates to a method for manufacturing alcohol or alcoholic beverage by fermenting maize or milomaize.

It has been a common practice that before fermenting cereals, the cereals are ground and mixed with water or a mixture of water and stillage to obtain mash, which is then heated to burst the starch cell and liquefy starch contained in cereals, followed by saccharification. Hitherto, for sufficient bursting and liquefaction of starch contained in cereals, there has been used cooking at temperatures of 115° to 180° C for 1 to 60 minutes under high pressure. In addition, before or after the above cooking, saccharification proceeds to some extent along with the liquefaction, due to the addition of acids or liquefying enzymes, for instance, germinated cereals or enzymes from microorganisms, thereby reducing the viscosity of the mash. The mash, in which starch has been liquefied and partially saccharified, is filtered, as required, and then cooled to an optimum fermentation temperature, such as 25° to 34° C, after which the saccharifying enzymes and alcohol fermentative yeasts are added for fermentation. Alternatively, the mash is cooled to the temperature optimum for saccharifying enzymes, such as 50° to 65° C, following the cooking step, then saccharifying enzymes are added, and a mixture thus obtained is held at the above temperature for a while for allowing further saccharification of starch. Then, the mixture is cooled to the fermenting temperature of 25° to 34° C for fermentation.

It is known as the best method for obtaining alcohol at a high yield to cook mash at a high temperature of nearly 150° C in the case of conventional cooking or of nearly 180° C in the case of continuous cooking under a high pressure in using maize or milomaize. The object to cook the cereals at a high temperature is to rupture the structures of cereal grits to elute starch from the cereal grits as well as to sterilize cereals. More particularly, upon the cooking of cereals, the corn exhibits the maximum viscosity in the temperature range of 90° to 95° C in the case of the use of maize and milomaize as shown in FIG. 1, although this temperature depends on the kinds of cereals. An increase of a temperature more than the maximum viscosity temperature causes a decrease in the viscosity of the mash. The prior art utilizes a decrease in viscosity due to such an increased temperature, for facilitating handling of the mash as well as for enhancing the liquefaction of starch and the action of saccharifying enzymes on starch. In addition, cooking at a high temperature has a sterilizing effect on undesirable type microorganisms. Thus, it has been widely accepted that cooking at a temperature lower than the aforesaid temperature range results in the failure to elute starch or in difficulty in agitation due to increased viscosity after gelatinization, which in turn brings about incomplete liquefaction and saccharification. This lowers the manufacturing yields i.e., the amount of alcohol to be manufactured.

It is an object of the present invention to provide a method for manufacturing alcohol or alcohol beverage which, by avoiding the high-temperature, high-pressure cooking step of the prior art, saves energy to be used, and the amount of cooling water, and which eliminates a danger in operation that stems from the operation using a high temperature and high pressure, and which lowers construction and maintenance costs of the equipment by the alteration from high pressure equipment to atmospheric pressure equipment.

According to the present invention, there is provided a method for manufacturing ethyl alcohol or alcoholic beverage, which comprises the steps of: adding water or a mixture of water and stillage, to grits of maize or milomaize containing grits of over 30% through 20 mesh to thereby obtain a slurry having 13 to 40% by weight of solid contents; heating the mash at a temperature 5° to 15° C lower than the temperature presenting the maximum viscosity, i.e. from 75° C. to 85° C., for the mash but higher than the sterilization temperature of undesirable type microorganisms, for the duration of 1 to 30 minutes under substantially atmospheric pressure, with or without liquefying enzymes being added; cooling the mash to 25° to 34° C and adding saccharifying enzymes and alcohol fermentative yeasts and distilling the fermented slurry thus obtained. As required, after heating at 75° C. to 85° C., the slurry thus heated may be cooled to 50° to 65° C, and then a saccharifying agent are added thereto, followed by standing at the aforesaid temperature for up to 30 minutes, and then cooling to 25° to 34° C, for the aforesaid fermentation.

FIG. 1 is a graph illustrative of the results of measurements of variation in viscosity of water suspension of grits of cereals as used in the comparative Example, at varying temperatures of water suspension.

The ground maize or milomaize as used herein may include the cereals themselves and grits of the cereals excluding embryo, and starch derived from the cereals. In addition, this may include a mixture of raw materials containing over 50% by weight of such ground cereals with other starchy materials. Included as cereals to be added to maize or milomaize are rice, barley, wheat, rye, barnyard millet, common millet and Italian millet and the like. In this respect, the finer the size of grits, the better will be the results. However, grits of over 30% through 20 mesh may suffice for this purpose, and water or a mixture of water and stillage is added to such grits to obtain a slurry having 13 to 40% by weight, of solid content. Meant by the term "stillage" is a residue of the mash, from which alcoholic components have been distilled after the completion of fermentation. The stillage in amounts of up to about 40% may be added thereto, with or without filtration. The temperature exhibiting the high viscosity due to the heating and the resulting gelatinization of mash of the aforesaid ground cereals varies depending on the kinds of cereals, lots and mash concentrations. It suffices if in the aforesaid mash concentration, the aforesaid temperature falls within the range of 90° to 95° C in the case of ground maize and milomaize, while the sterilization temperature of undesirable type microorganisms, which can grow violently in the slurry during fermentation and cause the decrease of alcohol yield, should fall within the range exceeding 70° C. The heating temperature according to the present invention should fall within the above temperature ranges, preferably 5° to 15° C lower than the temperature presenting the maximum viscosity, and more preferably between 75° and 85° C. Upon heating, a liquefying agent may be added to the slurry.

The use of the liquefying enzymes according to the present invention may include germinated cereals and liquefying enzymes preparations from microorganisms, for instance α-amylase from Bacillus SP, which are used alone or in combination. It suffices that the time required for heating at 75° C. to 85° C. is on the order of 1 to 30 minutes, as in the case of the prior art. Thereafter, the slurry is cooled to the fermenting temperature of 25° to 34° C, and then malts and/or saccharifying enzymes and alcohol fermentative yeasts are added to the mash. Depending on the case, the mash is cooled to 50° to 65° C after heating, then saccharifying enzymes or malts are added thereto, and a mixture thus prepared is held at the aforesaid temperature for up to 30 minutes for the progress of saccharification, after which the mixture may be cooled to 25° to 34° C, and then alcohol fermentative yeasts are added thereto for fermentation according to a known method. The use of the saccharifying enzymes according to the present invention may include germinated cereals (malts) and the saccharifying enzyme (e.g. glucoamylase from fungi) preparations derived from microorganisms, which are used alone or in combination. The fermentation is normally carried out at 25° to 34° C for 4 to 5 days, after which, if required, the mash is filtered, and then alcohol or alcoholic beverage may be obtained according to distillation.

As is apparent from the foregoing description, the structures of starch are partially changed according to the heating step. However, the method according to the present invention is not contemplated to rupture the starch structure completely, as in the prior art for gelatinization, but to effect the partial gelatinization, and then malts or saccharifying enzymes and alcohol fermentative yeasts are added for the subsequent fermentation. Stated otherwise, the structures of starch are partially transformed due to the heating at a temperature on the order of the sterilization temperature of undesirable type microorganisms, that is, from 75° C. to 85° C. This dispenses with cooking and sterilization at a temperature higher than 115° C, as in the prior art method, yet presents satisfactory fermentation.

On the other hand, it is known that starch is saccharified under the action of enzymes at a temperature of about 55° C, without liquefying the starch. This is possible, only when a special kind of cereals or special kind of enzymes is used. However, the use of direct saccharification of cereals at the temperature of about 55° C necessitates the sterilization of cereals by using chemicals or X-rays, beforehand, or the addition of chemicals for interrupting the propagation of undesirable type microorganisms or a method for interrupting the propagation of undesirable type microorganisms during the step of saccharification. Those methods however suffer from shortcomings in that their effects are not complete or they deteriomentally affect the organoleptic tests of final products.

As is disclosed in British patent No. 1,248,505, which corresponds to Netherlands patent application No. 6800875, filed Jan. 19, 1968, it is known that enzymes which tend to decompose cellulose, helicellulose and protein are brought into reaction with mash, at a temperature of 50° to 60° C for decomposition of same, after which starch is liquefied at a temperature of 86° to 88° C. This, however, uses the aforesaid gelatinization and complete liquefaction. According to the aforesaid Netherland patent application, the mash which has been completely liquefied is further saccharified, and then insoluble matter is filtered and condensed for obtaining a fermenting condensate or powder. In contrast thereto, the present invention is not contemplated to use complete gelatinization which brings about high viscosity, but malts and/or alcohol fermenting yeast and saccharifying enzymes are added to the slurry which has been subjected to incomplete liquefaction and saccharification, for fermentation.

The method according to the present invention is not contemplated to effect gelatinization and saccharification of starch, enabling the pretreatment such as heating at from 75° C. to 85° C. for a relatively short time period. In addition, the cooling step may be carried out continuously for facilitating the operation.

According to the prior art method, mash is cooked at a temperature over 115° C, normally 140° to 150° C, for liquefaction, after which the mash is cooled to a fermenting temperature according to a heat-exchangeable flash cooler, or by adding water and the like. In this respect, special equipment for recovery of heat used for heating is required, with the accompanying difficulty and, considerable degree of heat for cooking and amount of water for cooling is wasted. In contrast thereto, according to the method of the present invention, the cooking step which would have otherwise required the use of a high temperature, if resorted to the prior art, may be carried out at a lower temperature, thus saving the amounts of fuel, cooling water and the like to about half of the conventional amounts, while there may remain enzymes which are added in the mash before heating at from 75° C. to 85° C., for instance, liquefying enzymes contained in germinated cereals or from microorganisms, particularly α-amylase, which effectively may function throughout the entire period of conversion and fermentation, thereby preventing an increase in viscosity of the slurry as well as presenting desirable results of fermentation due to the high saccharifying ability to saccharifying enzymes. In addition, the active fermentation of yeasts retains the suppressing action against the propagation of undesirable type microorganisms, in addition to the total fermenting hours and fermentation efficiency which is obtained as well as according to the prior art.

The following examples are illustrative of the features of the method according to the present invention.

COMPARATIVE EXAMPLE

Measurements were given to the variation in viscosity at varying temperature increasing and decreasing rates, of water suspension containing five kinds of ground maizes (1) to (5) and ground milomaize (6) having varying qualities and varying lots, which are used for the low-temperature-cooking alcohol fermentation. FIG. 1 shows the results of measurements of variation in viscosity of slurry, which has been obtained by grinding cereals to particle size distribution of 80% through 20 mesh and 30% through 65 mesh, and suspending same in water to a concentration, at which solid contents are contained in amounts of 13% by weight. Then, the suspension was put in the Brabender Viscograph, wherein the slurry is heated under agitation from 40° C to 95° C at a temperature gradient of 1.5° C/min., after which the slurry is held at 95° C for 10 minutes, then the suspension is cooled to 40° C at the same temperature gradient. This graph reveals that the temperature presenting the highest viscosity during the temperature rise, ranges from 90° to 94° C in the case of three kinds of yellow dent maizes (1), (2), (3) excluding yellow flint maize (5), while the aforesaid temperature is 94° C in the case of milomaize. As can be seen from the graph showing the variation in viscosity, the temperature ranges below 90° C. to 94° C. do not provide a slurry of highest viscosity.

EXAMPLE 1

Yellow dent maize was ground to the five particle size levels as shown in Table 1, and the relationship between the heating temperature and the fermentation results were studied. More particularly, water was added to 100g of ground maizes so as to obtain a slurry containing 18% by weight of solid contents, and then 3g of malt powder was added as liquefying enzymes to the aforesaid slurry, which was allowed to stand for 30 minutes at a desired temperature (50° C, 60° C, 70° C, 75° C, 80° C, 120° C). Thereafter, the suspension was cooled to 28° C, and then 17g of malt powder and 0.1g of glucoamylase from Rhizopus SP. (800u/g JIS K 7001-1972) were added thereto, followed by addition of 25ml of culture yeast. Then, the slurry was brought into fermentation at 28° C for 72 hours and analyzed for comparison of fermentation results.

Table 1

| Particle size level Distribution of particle sizes | A | B | C | D | E |
|---|---|---|---|---|---|
| | (%) | (%) | (%) | (%) | (%) |
| 20 Mesh ON | 63.4 | 20.8 | 10.2 | 4.4 | 0 |
| 32 Mesh ON | 9.6 | 21.9 | 18.8 | 18.8 | 1.8 |
| 48 Mesh ON | 6.2 | 18.3 | 20.0 | 21.5 | 15.3 |
| 65 Mesh ON | 3.2 | 8.5 | 9.3 | 9.4 | 10.2 |
| 100 Mesh ON | 2.4 | 6.0 | 5.0 | 5.4 | 6.1 |
| 100 Mesh Pass | 15.2 | 24.5 | 36.7 | 40.5 | 66.6 |

As can be seen from Table 2, the finer the particle size, the lower temperature is obtained for the high fermentation efficiency (percentage of alcohol produced X the volume of fermented mash/total sugar as glucose X 0.6439), the same as the prior art. Even in case the large particle size such as size level A is used, if the slurry is heated at 75° C. for 30 minutes, the results are substantially equivalent. It is shown that, with particle sizes such as those of B through D, heating of the slurry at 75° C. provides good fermentation efficiency such as in the case of high temperature (120° C.) heating. It is further proved that the effect of undesirable type microorganisms is a function of a decrease in fermentation efficiency and a rise in the total acidity.

Table 2

| Particle size level | Heating temp. | PH | TA* | Fermentation efficiency (%) |
|---|---|---|---|---|
| A | 50° C | 3.7 | 7.0 | 66.6 |
| | 60 | 4.2 | 4.0 | 70.0 |
| | 70 | 4.5 | 3.0 | 76.5 |
| | 75 | 4.7 | 2.3 | 83.8 |
| | 80 | 4.8 | 2.3 | 84.6 |
| | 120 | 4.8 | 2.3 | 84.0 |
| B | 50 | 4.0 | 4.5 | 78.0 |
| | 60 | 4.3 | 3.9 | 81.5 |
| | 70 | 4.7 | 2.6 | 83.5 |
| | 75 | 4.7 | 2.1 | 84.6 |
| | 80 | 4.8 | 2.3 | 85.0 |
| | 120 | 4.7 | 2.3 | 85.0 |
| C | 50 | 4.1 | 4.0 | 82.0 |
| | 60 | 4.5 | 3.5 | 83.9 |
| | 70 | 4.7 | 2.4 | 84.8 |
| | 75 | 4.8 | 2.3 | 85.3 |
| | 80 | 4.7 | 2.3 | 85.5 |
| | 120 | 4.7 | 2.3 | 85.1 |
| D | 50 | 4.1 | 4.0 | 81.5 |
| | 60 | 4.5 | 3.2 | 83.5 |
| | 70 | 4.8 | 2.1 | 84.5 |
| | 75 | 4.7 | 2.1 | 85.3 |
| | 80 | 4.6 | 2.3 | 85.6 |
| | 120 | 4.7 | 2.1 | 85.5 |
| E | 50 | 4.2 | 3.8 | 82.0 |
| | 60 | 4.4 | 3.0 | 83.5 |
| | 70 | 4.7 | 2.3 | 84.2 |
| | 75 | 4.7 | 2.3 | 85.4 |
| | 80 | 4.8 | 2.3 | 85.5 |
| | 120 | 4.7 | 2.3 | 85.0 |

Table 2-continued

* TA: total acidity, milli liters of N/10 NaOH required for neutralizing 10 ml. of mash.

EXAMPLE 2

Water was added to 100g of various kinds of ground cereals of a size level B shown in Table 1 to obtain a slurry containing about 18% by weight of solid contents, after which 3g of malt powder as liquefying enzymes was added to the aforesaid slurry and agitated, followed by standing at 80° C for 30 minutes. Thereafter, the slurry was cooled to 28° C, and 17g of malt powder and 0.1g of glucoamylase (800u/g JIS K 7001-1972) were added, followed by further addition of 25 ml of culture yeast (*Saccharomyces cerevisiae*). The slurry was fermented at 28° C for 72 hours and analyzed for comparision of fermentation results. Table 3 shows the results of the analysis. This shows that there may be obtained fermentation efficiency of over 80%, presenting the same results as those obtained from the prior art fermentation which uses heating at a temperature of over 120° C. The measurements of viscosities of slurry obtained from the aforesaid cooking condition gives no difference to those of slurry which has been subjected to cooking at a temperature of over 120° C.

EXAMPLE 3

Water was added to 100g of two kinds of ground yellow dent maize and milomaize of a size level C in Table 1 to thereby obtain a slurry containing about 18% by weight of solid contents, and then the slurry was held at 75° C for 30 minutes. Thereafter, the slurry was cooled to 28° C, and then 17g of malt powder and 0.02g of glucoamylase (800u/g JIS K 7001-1972) were added, followed by the further addition of 25 ml of culture yeast. Then, the slurry was subjected to fermentation at 28° C for 96 hours, and analyzed for comparison of the results of fermentation. The results are shown in Table 4 which reveals that there may be obtained the fermentation results similar to these obtained from the prior art which uses cooking at 150° C for 30 minutes.

Solid contents were removed from the mash, after the completion of fermentation, and then the fermented liquid was distilled in a glass still for separating distillate of alcohol 20 to 30 Vol % therefrom, and then the distillate was again distilled in the same still to obtain distillate of alcohol 60 Vol %. The distillate or alcoholic beverage was compared with that obtained from the prior art which uses cooking at 150° C for 30 minutes, according to an organoleptic test, with the result of no noticeable difference.

Table 3

| Kinds of cereals | PH | TA | RTS | produced alcohol (%) | Fermentation efficiency (%) | Fermentation efficiency according to prior art (%) |
|---|---|---|---|---|---|---|
| Milomaize | 4.98 | 2.22 | 1.79 | 9.5 | 85.1 | 85.0 |
| Yellow dent maize[1] | 4.76 | 2.36 | 2.11 | 9.0 | 85.9 | 85.5 |
| Yellow dent maize[2] | 4.86 | 2.80 | 2.00 | 9.2 | 87.0 | 86.0 |
| Yellow dent maize[3] | 4.91 | 2.54 | 2.25 | 9.0 | 86.0 | 86.3 |

| Particle size level | Heating temp. | PH | TA* | Fermentation efficiency (%) |
|---|---|---|---|---|
| | 120 | 4.7 | 2.3 | 85.0 |

Table 3-continued

| Kinds of cereals | PH | TA | RTS | produced alcohol (%) | Fermentation efficiency (%) | Fermentation efficiency according to prior art (%) |
|---|---|---|---|---|---|---|
| Yellow flint maize | 4.98 | 2.54 | 2.18 | 9.0 | 86.6 | 85.2 |
| White dent maize | 4.91 | 2.42 | 2.11 | 9.3 | 89.4 | 86.5 |

(2)RTS: total residual sugars, gram as glucose/100g mash

Table 4

| Kinds of cereals | PH | TA | RTS | produced alcohol (%) | Fermentation efficiency (%) | Fermentation efficiency according to prior art (%) |
|---|---|---|---|---|---|---|
| Yellow dent maize | 4.75 | 2.81 | 2.05 | 9.2 | 85.7 | 86.0 |
| Milomaize | 4.86 | 2.50 | 1.98 | 9.5 | 86.6 | 85.0 |

EXAMPLE 4

Water was added to 2kg of ground yellow dent maize of the size level B shown in Table 1, from which the embryo portion has been removed, to thereby obtain a slurry containing 20% by weight of solid contents. Then, 9g of bacterial liquefying-α-amylase (4500u/g JIS K 7001-1972) was added as a liquefying enzyme under agitation and allowed to stand at 80° C for 10 minutes. Then, the slurry was cooled to 28° C, and then 2g of glucoamylase (800u/g JIS K 7001-1972) was added thereto, followed by further addition of 500ml of culture yeast. Then, the slurry was brought into fermentation at 28° C for 85 hours and analyzed for comparison for fermentation results. The results thus obtained are given in Table 5, presenting no appreciable difference to that obtained from the prior art.

Table 5

| PH | TA | RTS | produced alcohol(%) | Fermentation efficiency(%) | Fermentation efficiency according to prior art (%) |
|---|---|---|---|---|---|
| 4.3 | 2.0 | 1.80 | 8.3 | 85.0 | 85.1 |

EXAMPLE 5

Water was added to 2kg of corn starch obtained from maize to thereby obtain a slurry containing 18% solid contents, and then 30g of malt powder and 4g of bacterial a liquefying-amylase (4500u/g JIS K 7001-1972) as liquefying enzyme was added thereto under agitation and held at 80° C for 10 minutes. Thereafter, the aforesaid slurry was cooled to 28° C, and then 240g of malt powder added thereto, followed by the further addition of 500 ml of culture yeast for fermentation at 28° C for 85 hours. Then, the analysis was given for comparison of fermentation results, which are shown in Table 6, presenting almost the same fermentation efficiency as those obtained from the prior art.

Table 6

| PH | TA | RTS | produced alcohol(%) | Fermentation efficiency(%) | Fermentation efficiency according to prior art (%) |
|---|---|---|---|---|---|
| 4.4 | 2.7 | 1.58 | 9.2 | 83.5 | 83.2 |

EXAMPLE 6

Water was added to the ground yellow dent maize and milomaize of a size level B shown in Table 1, respectively, to obtain a slurry containing about 25% by weight of solid contents, after which 20g of bacterial liquefying amylase (4500u/g JIS K 7001-1972) as a liquefying enzyme was added thereto under agitation, and then held at 75° C for 10 minutes. Thereafter, the slurry was cooled to 28° C, and then 2.8g of glucoamylase (800u/g JIS K 7001-1972) was added thereto, followed by the further addition of 500 ml of culture yeast for fermentation at 28° C for 85 hours. Then, the analysis was given for comparison of fermentation results, which are shown in Table 7, presenting almost the same fermentation results as those obtained from the prior art.

Table 7

| Kinds of cereals | PH | TA | RTS | produced alcohol (%) | Fermentation efficiency (%) | Fermentation efficiency according to prior art (%) |
|---|---|---|---|---|---|---|
| Yellow dent maize | 4.73 | 3.08 | 2.53 | 11.3 | 88.5 | 86.0 |
| Milomaize | 4.68 | 2.75 | 2.60 | 12.1 | 86.3 | 86.8 |

EXAMPLE 7

Water was added to the ground yellow dent maize, white dent maize and milomaize of a size level B shown in Table 1, to obtain slurries containing about 20% by weight of solid contents, and then 0.0045g of bacterial liquefying amylase (4500u/g JIS K 7001-1972) per 1g of cereals on dry base was added as a liquefying enzyme under agitation and then the slurry was fed into continuous cooking pipes, while steam was being introduced into the resulting slurry to raise the temperature to 75° C by means of a heater. Under such conditions, the slurry was caused to flow through the continuous heating pipes for a distance of 36m at a speed of 0.6m/sec, and then cooled to 28° C by means of a heat exchangeable pipes. Thereafter, glucoamylase (800u/g JIS K 7001-1972) was added so as to give 0.46u/ml, after which the slurry was placed in a 10-liter glass fermenting tank (inner diameter 20cm), while yeast cells were added thereto so as to give $2 \times 10^6$ cells/ml of the slurry for fermentation at 28° C for 72 hours. The results are shown in Table 8, presenting the fermentation results similar to those obtained from the prior art.

Table 8

| Kinds of cereals | PH | TA | RTS | produced alcohol (%) | Fermentation efficiency (%) | Fermentation efficiency according to prior art (%) |
|---|---|---|---|---|---|---|
| yellow dent maize | 4.3 | 2.0 | 1.45 | 7.6 | 85.9 | 85.5 |

Table 8-continued

| Kinds of cereals | PH | TA | RTS | produced alcohol (%) | Fermentation efficiency (%) | Fermentation efficiency according to prior art (%) |
|---|---|---|---|---|---|---|
| White dent maize | 4.3 | 2.0 | 1.56 | 7.7 | 86.3 | 86.5 |
| Milomaize | 4.3 | 2.0 | 1.60 | 7.7 | 86.0 | 85.0 |

EXAMPLE 8

Water and stillage (70:30) were added to the raw materials consisting of 80% by weight of yellow dent maize which have a grit-size level A shown in Table 1 and 20% by weight of rice starch, thereby obtaining slurries containing about 28% by weight of solid contents. Then, 0.0045g of bacterial liquefying amylase (4500u/g JIS K 7001-1972) per 1g on dry basis of the raw materials as a liquefying enzyme was added thereto under agitation, and fed into continuous heating pipes, while steam was introduced therein by means of an heater to raise the temperature of the slurry to 80° C. Then, at this temperature, the slurry was caused to flow through the heating pipes at a speed of 0.6m/sec for a distance of 36m and then through heat-exchange pipes so as to bring the temperature of the slurry to 60° to 65° C, whereupon a slurry of malt powder was introduced so as to give 0.2g of malt per 1g on dry basis of the raw materials, and then held at 60° to 65° C for 10 minutes, followed by cooling to 28° C. After cooling, the slurry was placed in a 100-liter fermenting tank, and then glucoamylase (800u/g JIS K 7001-1972) was added so as to give 0.05u/ml, followed by further addition of yeast so as to give 2×10⁶ cells/ml of the slurry, for fermentation at 28° C for 85 hours. Table 9 compares the analyzed values and fermentation efficiency of the mash after fermentation, with those obtained from the prior art, presenting almost the same results for the both cases.

The aforesaid mash was distilled in an ordinary type continuous still, thereby obtaining distillate of 95.5 Vol% alcohol. On the other hand, in case there is obtained alcohol is beverage containing 65 Vol% alcohol according to the conventional method, the quality is proved to be well comparable to that of the prior art distillate.

Table 9

| | This invention | prior art |
|---|---|---|
| PH | 4.1 | 4.0 |
| TA | 3.7 | 4.0 |
| RTS | 1.03 | 1.09 |
| produced alcohol | 9.0 | 9.0 |
| fermentation efficiency | 85.9 | 85.7 |

EXAMPLE 9

Water and stillage (80:20) were added to ground yellow dent maize of a size level B shown in Table 1 so as to obtain a slurry containing about 33% by weight of solid contents, and then 0.0045g of bacterial amylase (4500u/g JIS K 1972) was added to maize per 1g of maize (on dry basis) under agitation, and then introduced into continuous heating pipes, with steam being introduced through an heater so as to raise the temperature of the slurry to 80° C. Then, the slurry was caused to flow through the continuous heating pipes at the aforesaid temperature at a speed of 0.6m/sec for a distance of 150m, and then cooled to 28° C by means of heat exchange pipes. Thereafter, glucoamylase (800u/g JIS K 7001-1972) was added so as to give 0.17u/ml and then the slurry was placed in 120kl fermenting tank, and then yeast cells precultured were added so as to give 2×10⁶ cells/ml of the slurry for fermentation at 28° C for 72 hours. Table 10 compares the analyzed values of fermentation efficiency of the mash after the completion of fermentation. The titration acid and PH shown tell that there is no damage due to undesirable type microorganisms as in the case of the prior art and the fermentation efficiency as well remain the same. The mash after completion of such fermentation was distilled in an ordinary type still, thereby obtaining a distillate of 95.5% alcohol. On the other hand, in case there is obtained an alcoholic beverage containing 65 Vol% alcohol according to the prior art, no difference in quality results.

Table 10

| | This invention | prior art |
|---|---|---|
| PH | 4.0 | 4.0 |
| TA | 2.9 | 2.8 |
| RTS | 0.80 | 0.77 |
| produced alcohol (%) | 8.5 | 8.3 |
| fermentation efficiency (%) | 87.1 | 86.7 |

The aforesaid nine examples are compared with the case of cooking at 140° C, with respect to energy used, presenting saving half the energy and amount of cooling water, as compared with the prior art.

The aforegoing information and examples are presented herein for illustrative purposes only and are not intended to unduly limit the scope of the invention.

What is claimed is:

1. A method for manufacturing alcohol or an alcoholic beverage, consisting essentially of the sequential steps of:
   (a) adding water or a mixture of water and stillage to (i) ground maize or (ii) milomaize, or to (III) ground maize or (IV) milomaize in admixture with ground cereal selected from the group consisting of rice, barley, wheat, barnyard millet, common millet and Italian millet, over 30% of which pass through 20 mesh, to obtain a slurry containing from 13 to 40% by weight of solid contents;
   (b) heating said slurry with malt or an α-amylase-containing liquefying enzyme preparation from microorganisms or a mixture thereof at a temperature of from 75° C. to 85° C. which is lower than the temperature of maximum viscosity for the slurry and which is higher than the sterilization temperature of undesirable microorganisms therein which can grow during yeast fermentation, and maintaining said slurry at said temperature of from 75° C. to 85° C. for from 1 to 30 minutes to cause incomplete liquefaction and partial gelatinization of starch therein;
   (c) cooling said slurry to a temperature of from 25° C. to 34° C.;
   (d) adding malt or a glucoamylase-containing saccharifying enzyme preparation from a microorganism or a mixture thereof, and an alcohol fermentative yeast to said cooled slurry;
   (e) fermenting the resulting slurry; and
   (f) distilling the resulting fermented mash; wherein at least said α-amylase-containing liquefying enzyme preparation is present in (b) or said glucoamylase-containing saccharifying enzyme preparation is present in (d).

2. The method as defined in claim 1, wherein said maize is in the form of ground maize grits from which the embryo has been removed.

3. The method as defined in claim 1, wherein said ground maize is in the form of starch derived from maize.

4. The method as defined in claim 1, wherein said admixture of (III) or (IV) is formed and consists essentially of a mixture of raw starchy materials over 50% by weight of which is derived from said maize or milomaize and the balance of which is derived from said ground cereal.

5. The method as defined in claim 1, wherein said ground maize is in the form of ground maize grits from which the embryo has been removed.

6. The method as defined in claim 1, wherein said ground maize is in the form of starch derived from maize.

7. The method for manufacturing alcohol or an alcoholic beverage, consisting essentially of the sequential steps of:
(a) adding water or a mixture of water and stillage to (i) ground maize or (ii) milomaize, or to (III) ground maize or (IV) milomaize in admixture with ground cereal selected from the group consisting of rice, barley, wheat, barnyard millet, common millet and Italian millet, over 30% of which pass through 20 mesh, to obtain a slurry containing from 13 to 40% by weight of solid contents;
(b) heating said slurry with malt or an α-amylase-containing liquefying enzyme preparation from microorganisms or a mixture thereof at a temperature of from 75° C. to 85° C. which is lower than the temperature of maximum visocosity for the slurry and which is higher than the sterilization temperature of undersirable microorganisms therein which can grow during yeast fermentation, and maintaining said slurry at said temperature of from 75° C. to 85° C. for from 1 to 30 minutes to cause incomplete liquefaction and partial gelatinization of starch therein;
(c) cooling said slurry to a temperature of from 50° C. to 65° C.;
(d) adding thereto malt or a glucoamylase-containing saccharifying enzyme preparation from a microorganism or a mixture thereof, and maintaining said slurry at said temperature of from 50° C. to 65° C. for up to 30 minutes;
(e) cooling said slurry to a temperature of from 25° C. to 34° C.;
(f) adding an alcoholic fermentative yeast to the cooled slurry;
(g) fermenting the resulting slurry; and
(h) distilling the resulting fermented mash; wherein at least said α-amylase-containing liquefying enzyme preparation is present in (b) or said glucoamylase-containing saccharifying enzyme preparation is present in (d).

8. The method as defined in claim 7, wherein said admixture of (III) or (IV) is formed and consists essentially of a mixture of raw starchy materials over 50% by weight of which is derived from said maize or milomaize and the balance of which is derived from said ground cereal.

* * * * *